(12) United States Patent
Park et al.

(10) Patent No.: US 10,549,018 B2
(45) Date of Patent: Feb. 4, 2020

(54) DEVICE FOR HARVESTING, PROCESSING AND TRANSFERRING ADIPOSE TISSUE

(71) Applicant: LifeCell Corporation, Madison, NJ (US)

(72) Inventors: Sangwook Park, Dunellen, NJ (US); Jerome Connor, Westminster, CO (US); Aaron Barere, Hoboken, NJ (US)

(73) Assignee: LIFECELL CORPORATION, Madison, NJ (US)

( * ) Notice: Subject to any disclaimer, the term of this patent is extended or adjusted under 35 U.S.C. 154(b) by 0 days.

(21) Appl. No.: 16/379,021

(22) Filed: Apr. 9, 2019

(65) Prior Publication Data
US 2019/0231947 A1 Aug. 1, 2019

Related U.S. Application Data

(60) Division of application No. 15/013,111, filed on Feb. 2, 2016, now Pat. No. 10,300,183, which is a continuation of application No. 13/894,912, filed on May 15, 2013, now Pat. No. 9,278,165.

(60) Provisional application No. 61/653,011, filed on May 30, 2012.

(51) Int. Cl.
| | |
|---|---|
| *G01N 1/36* | (2006.01) |
| *C40B 60/14* | (2006.01) |
| *A61K 35/12* | (2015.01) |
| *A61M 1/00* | (2006.01) |
| *A61M 5/00* | (2006.01) |

(52) U.S. Cl.
CPC ........ *A61M 1/0094* (2014.02); *A61M 1/0005* (2013.01); *A61M 1/0056* (2013.01); *A61M 1/0058* (2013.01); *A61M 5/00* (2013.01); *A61M 2202/08* (2013.01); *A61M 2205/75* (2013.01)

(58) Field of Classification Search
USPC ....... 422/68.1, 534, 535, 536, 547; 436/174, 436/175, 177, 178; 435/308.1, 325; 210/348; 424/520; 604/4.01, 6.09, 319, 604/540, 542
See application file for complete search history.

(56) References Cited

U.S. PATENT DOCUMENTS

| | | | |
|---|---|---|---|
| 3,993,067 A | 11/1976 | Schachet et al. | |
| 4,681,571 A | 7/1987 | Nehring | |
| 4,753,634 A | 6/1988 | Johnson | |
| 4,870,975 A | 10/1989 | Cronk et al. | |
| 4,898,572 A | 2/1990 | Surugue nee Lasnier et al. | |
| 5,049,273 A | 9/1991 | Knox | |

(Continued)

FOREIGN PATENT DOCUMENTS

| | | |
|---|---|---|
| CA | 2469370 | 7/2003 |
| CA | 2469370 A1 | 7/2003 |

(Continued)

OTHER PUBLICATIONS

U.S. Appl. No. 13/894,912, filed May 15, 2013, U.S. Pat. No. 9,278,165, Issued.

(Continued)

*Primary Examiner* — Dean Kwak
(74) *Attorney, Agent, or Firm* — McCarter & English, LLP

(57) ABSTRACT

The present disclosure provides devices and methods for harvesting and processing tissue from patients for grafting. The devices can include a tissue collection chamber for ascetically collecting, processing, and/or re-implanting adipose tissue.

13 Claims, 6 Drawing Sheets

(56) References Cited

U.S. PATENT DOCUMENTS

| | | |
|---|---|---|
| 5,055,198 A | 10/1991 | Shettigar |
| 5,301,685 A | 4/1994 | Guirguis |
| 5,624,418 A | 4/1997 | Shepard |
| 5,645,540 A | 7/1997 | Henniges et al. |
| 5,713,879 A | 2/1998 | Schneider |
| 5,785,640 A | 7/1998 | Kresch et al. |
| 5,823,986 A | 10/1998 | Peterson |
| D401,336 S | 11/1998 | Muller et al. |
| 5,901,717 A | 5/1999 | Dunn et al. |
| 6,017,493 A | 1/2000 | Cambron et al. |
| D424,194 S | 5/2000 | Holdaway et al. |
| 6,258,054 B1 | 7/2001 | Mozsary et al. |
| 6,325,788 B1 | 12/2001 | McKay |
| 6,623,733 B1 | 9/2003 | Hossainy et al. |
| 6,733,537 B1 | 5/2004 | Fields et al. |
| D492,995 S | 7/2004 | Rue et al. |
| D575,393 S | 8/2008 | Stephens |
| 7,588,732 B2 | 9/2009 | Buss |
| 7,595,043 B2 | 9/2009 | Hedrick et al. |
| 7,651,684 B2 | 1/2010 | Hedrick et al. |
| 7,744,820 B2 | 6/2010 | Togawa et al. |
| 7,780,649 B2 | 8/2010 | Shippert |
| 7,789,872 B2 | 9/2010 | Shippert |
| 7,794,449 B2 | 9/2010 | Shippert |
| 8,062,286 B2 | 11/2011 | Shippert |
| 8,100,874 B1 | 1/2012 | Jordan et al. |
| 8,293,532 B2 | 10/2012 | Moynahan |
| 8,333,740 B2 | 12/2012 | Shippert |
| D679,011 S | 3/2013 | Kitayama et al. |
| 8,409,860 B2 | 4/2013 | Moynahan |
| D683,851 S | 6/2013 | Greenhalgh |
| D687,549 S | 8/2013 | Johnson et al. |
| D692,559 S | 10/2013 | Scheibel et al. |
| 8,622,997 B2 | 1/2014 | Shippert |
| 8,632,498 B2 | 1/2014 | Rimsa et al. |
| 8,858,518 B2 | 10/2014 | Schafer et al. |
| 9,278,165 B2 | 3/2016 | Park et al. |
| 9,581,942 B1 | 2/2017 | Shippert |
| 10,300,183 B2 | 5/2019 | Park et al. |
| 2002/0188280 A1 | 12/2002 | Nguyen et al. |
| 2003/0161816 A1 | 8/2003 | Fraser et al. |
| 2004/0005246 A1 | 1/2004 | Efthimiadis et al. |
| 2005/0084961 A1 | 4/2005 | Hedrick et al. |
| 2006/0184119 A1 | 8/2006 | Remde et al. |
| 2006/0224144 A1 | 10/2006 | Lee |
| 2007/0106208 A1 | 5/2007 | Uber et al. |
| 2008/0209709 A1 | 9/2008 | Mayer |
| 2009/0181104 A1 | 7/2009 | Rigotti et al. |
| 2009/0287190 A1 | 11/2009 | Shippert |
| 2009/0299328 A1 | 12/2009 | Mudd et al. |
| 2010/0174162 A1 | 7/2010 | Gough et al. |
| 2010/0268189 A1 | 10/2010 | Byrnes et al. |
| 2010/0285521 A1 | 11/2010 | Vossman et al. |
| 2011/0009822 A1 | 1/2011 | Nielsen |
| 2011/0198353 A1 | 8/2011 | Tsao |
| 2013/0131635 A1 | 5/2013 | Rimsa et al. |
| 2013/0150825 A1 | 6/2013 | Rimsa et al. |
| 2013/0158515 A1 | 6/2013 | Austen, Jr. |

FOREIGN PATENT DOCUMENTS

| | | |
|---|---|---|
| CA | 2750498 | 6/2012 |
| CA | 2750498 A1 | 6/2012 |
| WO | 2009/055610 A1 | 4/2009 |
| WO | 2012/019103 A2 | 2/2012 |
| WO | 2012/083412 A1 | 6/2012 |
| WO | 2012/109603 A1 | 8/2012 |
| WO | 2012/139593 A2 | 10/2012 |

OTHER PUBLICATIONS

U.S. Appl. No. 15/013,111, filed Feb. 2, 2016, U.S. Pat. No. 10,300,183, Issued.

Coleman et al., Fat grafting to the breast revisited: safety and efficacy. Plast Reconstr Surg. Mar. 2007;119(3):775-85.

Delay et al., Fat injection to the breast: technique, results, and indications based on 880 procedures over 10 years. Aesthet Surg J. Sep.-Oct. 2009;29(5):360-76.

Pakhomov et al., Hydraulically coupled microejection technique for precise local solution delivery in tissues. J Neurosci Methods. Sep. 15, 2006;155(2):231-40.

Smith et al., Autologous human fat grafting: effect of harvesting and preparation techniques on adipocyte graft survival. Plast Reconstr Surg. May 2006;117(6):1836-44.

Ting et al., A new technique to assist epidural needle placement: fiberoptic-guided insertion using two wavelengths. Anesthesiology. May 2010;112(5):1128-35.

Yoshimura et al., Cell-assisted lipotransfer for cosmetic breast augmentation: supportive use of adipose-derived stem/stromal cells. Aesthetic Plast Surg. Jan. 2008;32(1):48-55.

International Preliminary Report on Patentability for Application No. PCT/US2013/041111, dated Dec. 11, 2014.

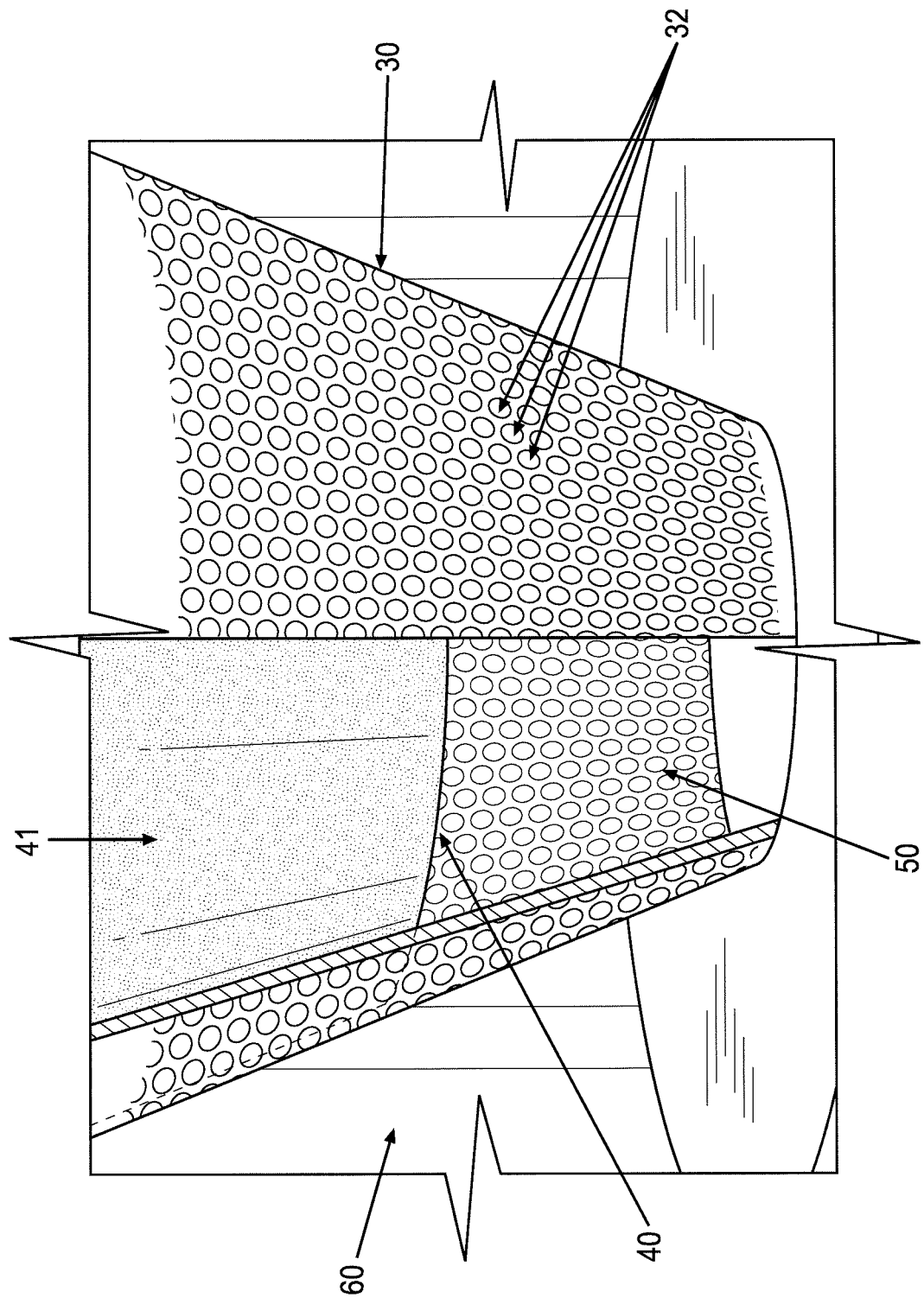

DEVICE FOR HARVESTING, PROCESSING AND TRANSFERRING ADIPOSE TISSUE

This application is a divisional of U.S. patent application Ser. No. 15/013,111, filed Feb. 2, 2016; which is a continuation of U.S. patent application Ser. No. 13/894,912 filed May 15, 2013 and issued as U.S. Pat. No. 9,278,165; which claims the priority of U.S. Provisional Application No. 61/653,011, filed May 30, 2012; all three applications of which are incorporated herein by reference in their entirety.

The present disclosure relates generally to devices and methods for harvesting and cleaning tissue.

Autologous fat transfer is a procedure that involves harvesting a patient's adipose tissue for implantation elsewhere in the patient's body. Adipose-tissue grafting involves a number of steps, which can include: collecting, processing, and/or implantation of the tissue. These steps may require fat to be transferred between instruments, which can present risks for infection, contamination, and tissue damage.

Accordingly, the present disclosure provides improved devices and methods for collecting, processing, and/or reimplanting adipose tissue and/or other tissue types.

SUMMARY

A device for preparing tissue is provided. The device can comprise a container and a filter having a peripheral rim portion, wherein the filter is positioned within the container such that the peripheral rim portion engages at least one inner surface of the container to define a first tissue collection chamber and a second filtrate collection chamber. The device can further comprise a flexible membrane, wherein the edges of the flexible membrane are connected to at least one of an inner surface of the container within the peripheral rim portion and the peripheral rim portion of the filter to form a fluid-tight seal between at least a part of the at least one inner surface and the first tissue collection chamber.

In certain embodiments, methods for preparing tissue are provided. The methods can comprise transferring tissue from a patient to a device for harvesting, processing, and/or transferring tissue. The device can comprise a container and a filter having a peripheral rim portion, wherein the filter is positioned within the container such that the peripheral rim portion engages at least one inner surface of the container to define a first tissue collection chamber and a second filtrate collection chamber. The device can further comprise a flexible membrane, wherein the edges of the flexible membrane are connected to at least one of an inner surface of the container within the peripheral rim portion and the peripheral rim portion of the filter to form a fluid-tight seal between at least a part of the at least one inner surface and the first tissue collection chamber. The method can further comprise processing the tissue and causing the flexible membrane to expand within the tissue collection chamber to apply pressure to the tissue within the first tissue collection chamber to transfer the tissue out of the tissue collection chamber. The method can further permit the re-injection of treated tissue into the delivery instrument at a constant pressure, thus reducing damage to the cells caused by the increase of shear forces in the cannula.

DESCRIPTION OF THE DRAWINGS

FIG. 2A illustrates a cut-away view of a device for processing tissue, according to certain embodiments of the present disclosure.

DESCRIPTION OF ILLUSTRATIVE EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the end points.

In certain embodiments, the present disclosure provides devices and methods for collecting, cleaning, concentrating, and/or preparing adipose tissue and/or other tissue types for implantation. The devices and methods can reduce the risk of contamination and complications related to tissue-graft surgery. The devices and methods can provide a single system for harvesting and processing of adipose tissue, which helps reduce surgical time, improves processed tissue quality, and reduces the risk of complications such as infection and/or graft failure. In certain embodiments, the devices provide a single container to aseptically collect, clean, concentrate, and/or transfer tissues.

Assemblies incorporating the devices and methods of use for aseptically harvesting, processing, and/or transferring processed tissue for implantation are also disclosed. The devices may be particularly useful for collecting, processing, and/or implanting adipose tissue, but the devices may have applicability for other tissues and/or tissue substitutes (e.g., processed tissue matrices, collagenous materials, and cellular compositions.)

Figure 1:
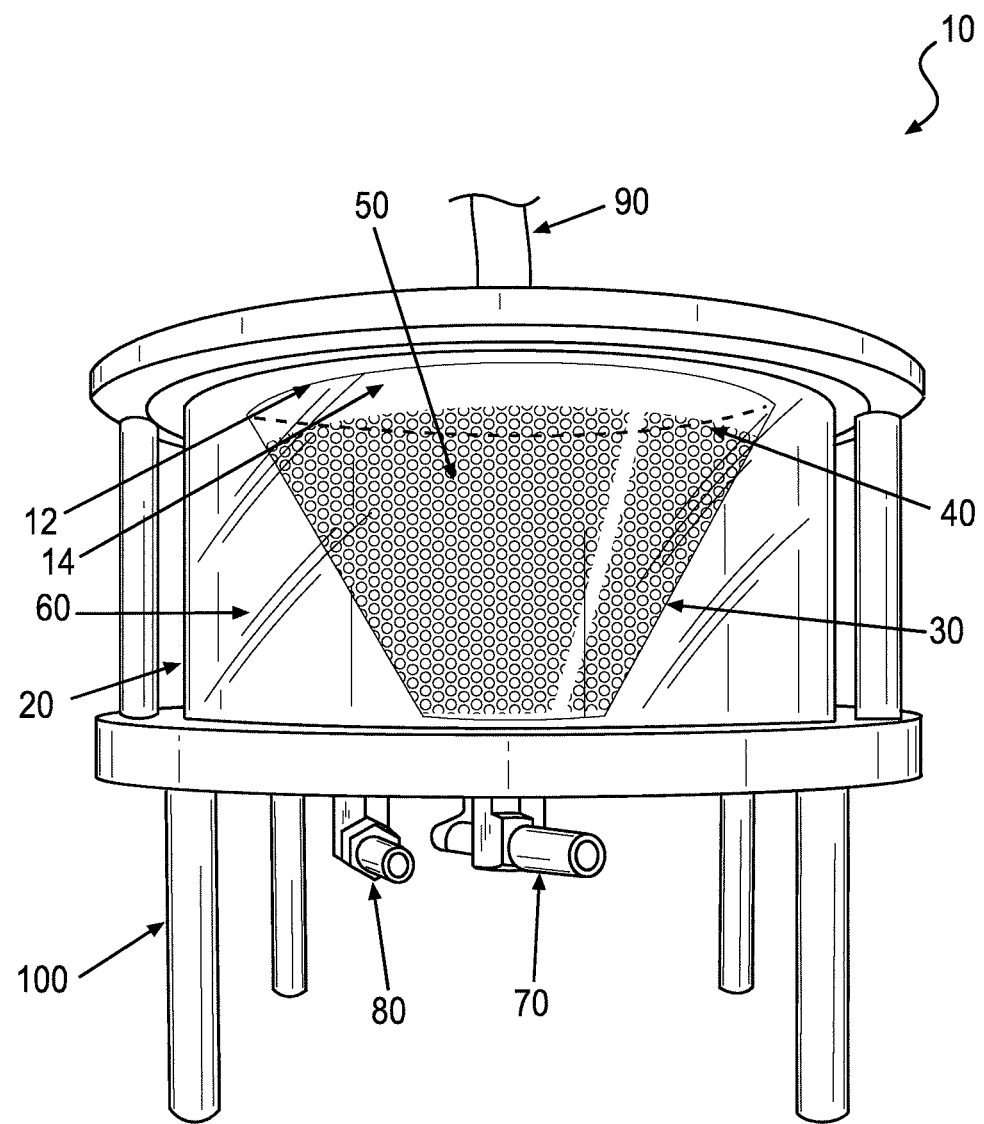
FIG. 1 illustrates a perspective view of a device for processing tissue, according to certain embodiments of the present disclosure.

In one aspect, as shown in FIG. 1, the present disclosure is directed to a device 10 for collecting, cleaning, concentrating, and/or transferring tissue. The device 10 can comprise a container 20 and a filter 30 having a peripheral rim portion 12. The filter 30 can be positioned within the container 20 such that the peripheral rim portion 12 engages at least one inner surface 14 of the container 20 to define a first tissue collection chamber 50 within the filter 30 and a second filtrate collection chamber 60.

As discussed further below, the device 10 can include one or more ports 70, 80. At least one port 70 can be in fluid communication with the tissue collection chamber 50. In some embodiments, an opening 74 (FIG. 2b) of the port 70 is within the tissue collection chamber 50. During use, tissue may be drawn into the tissue collection chamber 50 through the port 70 and may be subsequently pushed out of the port 70 for reimplantation. Further, a second port 80 is in fluid communication with the filtrate collection chamber 60 and can be attached to a suction line to allow removal of fluids or undesirable materials from tissue collected in the tissue collection chamber 50. In some embodiments, an opening 84 (FIG. 2B) of the port 80 is within the filtrate collection chamber 60.

The device 10 can further include a flexible membrane 40 (illustrated in FIG. 2A), which can assist in transferring tissue out of the tissue collection chamber 50. The flexible membrane 40 can also assist in removing excess fluid or other undesirable materials from the tissue contained in the tissue collection chamber 50. The flexible membrane 40 can be positioned within the tissue collection chamber 50 such that the edges of the flexible membrane 40 are connected to at least one of an inner surface 14 of the container within the peripheral rim portion 12 and the peripheral rim portion 12 of the filter 30 to form a fluid-tight seal between at least a part of the at least one inner surface 14 and the first tissue collection chamber 50. In some embodiments, the at least one inner surface 14 of the container or filter rim portion 12 may have an O-ring or similar component for sealing the edges. In various embodiments, the flexible membrane 40 can be connected directly to the filter rim portion 12, to the wall of the container within the filter's interior volume, to both the filter rim portion 12 and the wall of the container, or to other supporting structures within the container.

In certain embodiments, the membrane 40 is made of a flexible biocompatible material. For example, the membrane 40 can made of an elastomeric material that expands during use, as described further below. Non-limiting examples of suitable materials include silicone, and thermoplastic elastomers.

The container 20 can have a variety of suitable sizes, shapes, and structural features. The container 20 may have a shape and volume that allow for the placement of a filter 30 inside, while providing sufficient space to allow collection of filtrate resulting from the processing and/or washing of the tissue within the tissue collection chamber 50. In certain embodiments, the container 20 may be cubically or cylindrically shaped.

The container 20 can also be formed of a variety of different materials. Generally, the container 20 will be made of materials designed to withstand changes in pressure associated with processing tissue. In certain embodiments, the container 20 may be made of biocompatible and/or medical grade materials that can be sterilized as-needed. In certain embodiments, at least a portion of the container 20 is transparent such that device operators may visually inspect the contents of the device 10 during operation. Non-limiting examples of materials suitable for the container 20 include glass, polycarbonate, polypropylene, polyethylene, styrene, stainless steel or titanium, chrome plate on any metal and rigid plastics. In certain embodiments, the device 10 may be configured such that it is elevated from the ground or working surface by legs 100 or similar elevation mechanisms, such that hoses, cannulae, tubing or similar parts may be attached to ports 70, 80.

As discussed above, the device 10 can further include a filter 30. The filter may have a shape and volume that allow for its placement within the container 20, while providing sufficient space to allow collection of the tissue and fat cells being processed and/or washed. In certain embodiments, the filter holds volumes ranging from about 50 cubic centimeters to about 2000 cubic centimeters. The filter 30 may be selected to have openings or pores 32 (FIG. 2A) sized to retain collected tissue within the tissue collection chamber 50, while simultaneously allowing the removal of excess liquids and undesirable materials through the filtrate collection chamber 60. In certain embodiments, the size of the openings or pores are selected to allow the retention of viable groupings of adipose cells, while simultaneously allowing smaller components of the lipoaspirate, for example blood, free lipids, tumescent, wash solutions, collagen strands, and bust cells pass. In certain embodiments, the openings have a size ranging from 100 μm to 3 mm. In certain embodiments, the openings 32 are of the same or different sizes. In one embodiment, the filter may be a rigid mesh screen.

The filter 30 may be made of a rigid material designed to withstand pressures and/or pressure changes associated collecting, processing, and/or transferring tissues. In certain embodiments, the filter 30 may be made of biocompatible and/or medical grade material. Non-limiting examples of materials suitable for the filter 30 include metals, alloys, ceramics, and plastics. In one embodiment, the filter 30 is made of stainless steel.

Figure 2B:
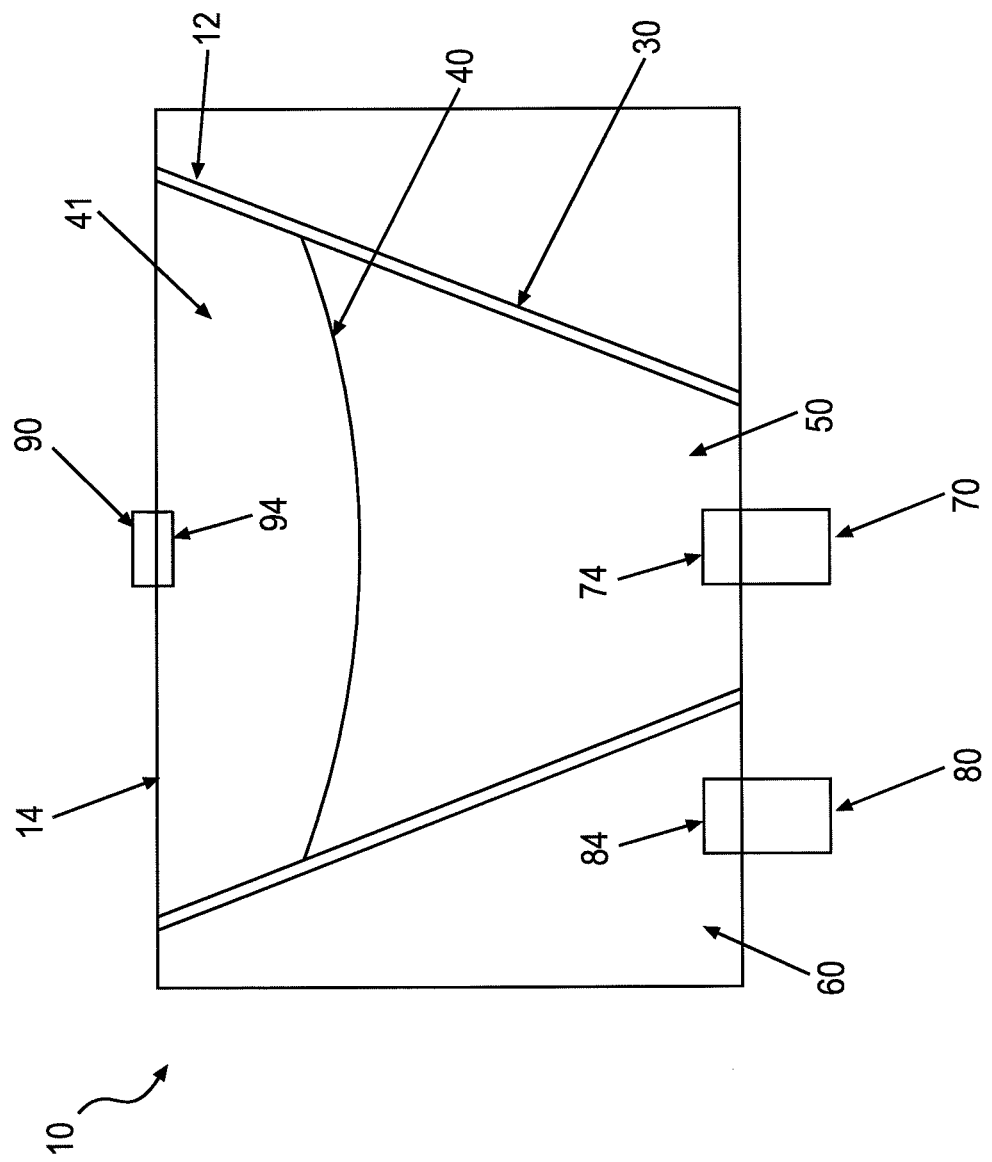
FIG. 2B illustrates a cross-sectional view of a device for processing tissue, according to certain embodiments of the present disclosure.
Figure 3:
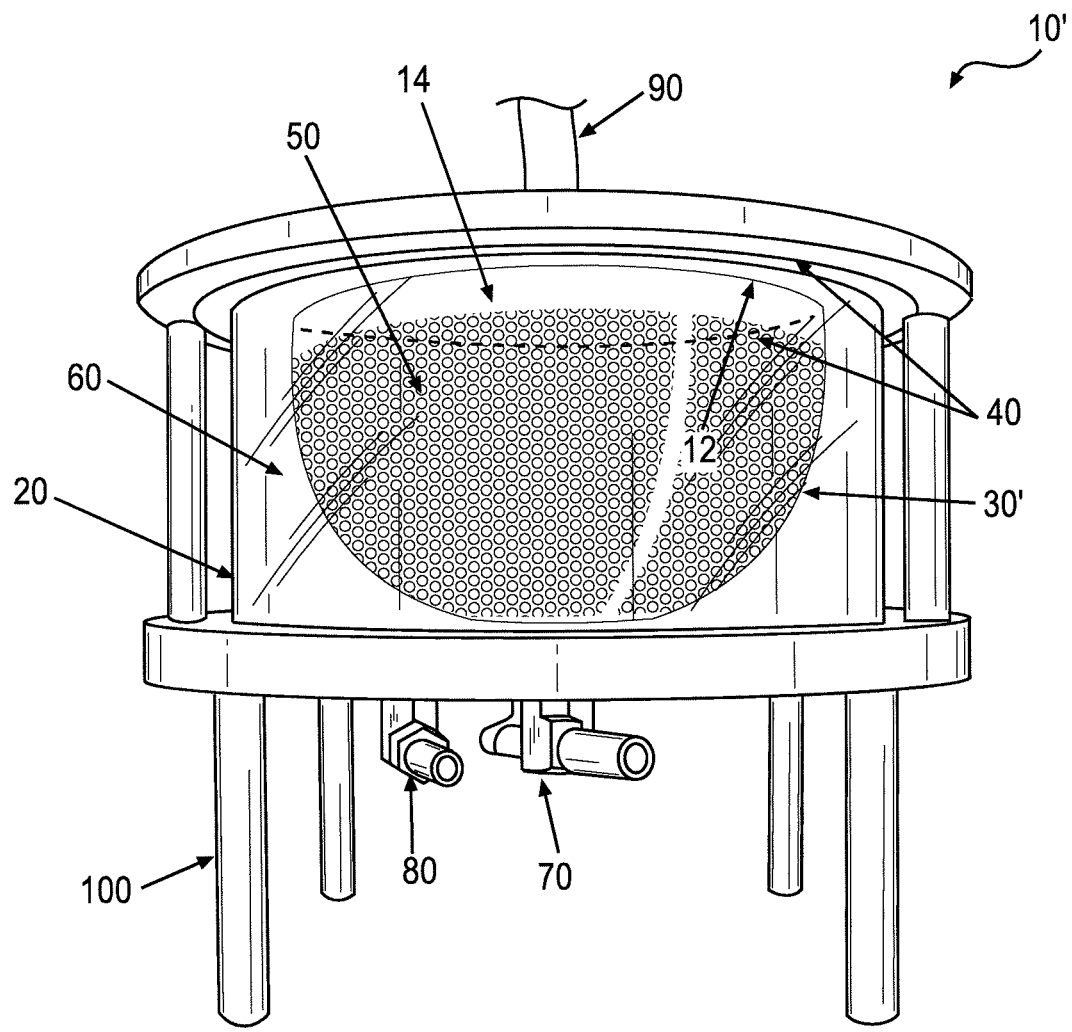
FIGS. 3 and 4 illustrate perspective views of two devices with alternative filter shapes, according to certain embodiments of the present disclosure.

In certain embodiments, the shape of the filter is selected such that its surface area in contact with the tissue is maximized to reduce clogging. In most embodiments, the filter is sized such that viable groupings of adipose cells are maintained and smaller components of the lipoaspirate (blood, free lipids, tumescent, wash solutions, collagen strands, bust cells) pass through the filter. For example, in certain embodiments the filter may have pores ranging from about 100 μm to about 3 mm pore size. The filter 30 can be shaped to assist in transfer of tissue out of the tissue collection chamber 50 and/or to assist in washing of tissue and/or removal of fluid (e.g., water from collected tissues). For example, in one embodiment, the filter 30 is shaped to guide the tissue within the tissue collection chamber 50 toward an opening 74 (FIG. 2B) of the port 70 to aid the transfer of tissue for implantation. The filter 30 can be shaped such that its cross-sectional area decreases towards the opening 74 of port 70. As such, the decreasing cross-sectional area guides the tissue and/or cells towards the opening 74 for removal from the tissue collection chamber 50. In certain embodiments, the filter 30 has a conical shape with a cross-sectional area that decreases towards the opening 74 of the port 70. In certain embodiments, the filter 30 is connected to the port 70 adjacent to the bottom of the device 10 to allow the introduction and removal of tissues. Other suitable shapes may be selected to facilitate transfer of tissue through the opening 74. For example, as shown in FIG. 3, the filter 30' may have a round bottom, but the filter can also be pyramidal, V-shaped, or have varying surface geometries.

Figure 4:
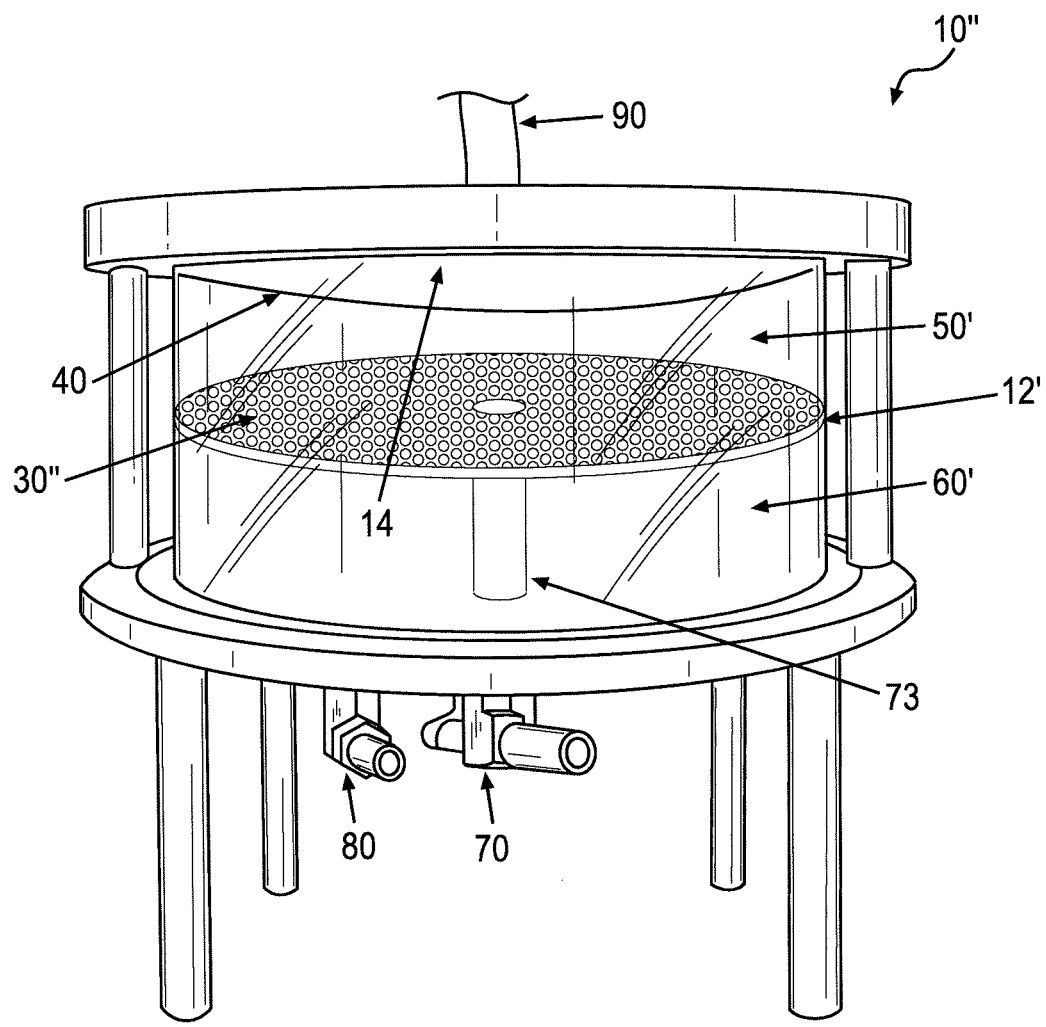

In addition, other filter shapes may be used. For example, as shown in FIG. 4, the filter 30" can be discoidal, or substantially flat. In embodiments according to FIG. 4, the tissue collection chamber 50' is in fluid communication with port 70 by a connecting tube 73. The connecting tube 73 may have a shape and volume that allow for the transfer of tissue in and out of the tissue collection chamber 50'. The tube 73 can be made of a material that can withstand pressure changes typical of the methods according to the present disclosure. The tube 73 and the port 70 may be made of biocompatible materials. In certain embodiments according to FIG. 4, the flexible membrane 40 can be connected directly to the wall of the container within the filter's interior volume.

As mentioned above, the devices of the present disclosure can further include a number of ports suitable for the transfer of tissue in and out of the device 10. The ports 70, 80 are suited with fittings made of biocompatible and/or medical grade materials that may withstand the pressure, temperature, flow rate and other process specifications. The ports can also be selected to allow the application of vacuum at different times during the process. The size of the ports is selected to allow the removal of unwanted materials from the device.

Figure 5:
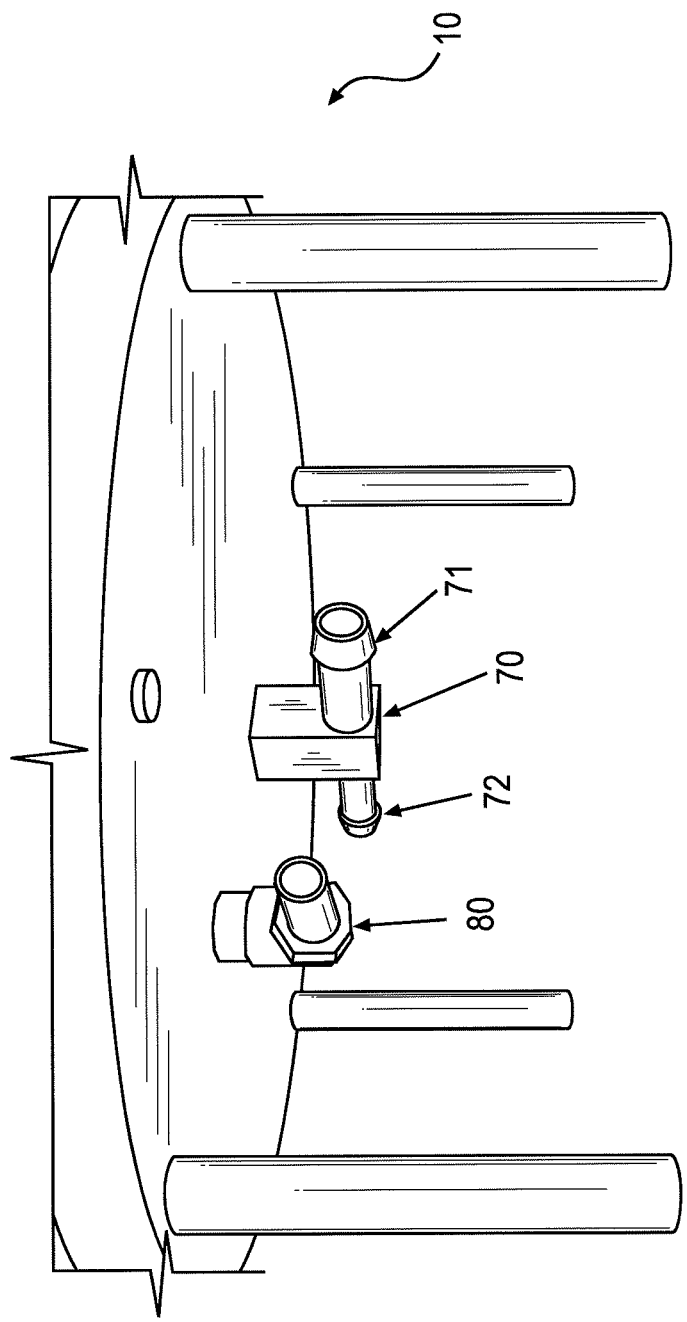
FIG. 5 illustrates an enlarged view of a portion of a device for processing tissue, according to certain embodiments of the present disclosure.

The present disclosure further provides methods for collecting, processing, and/or transferring tissue using the devices and any of their variations, as described herein. During use, medical tubing may be attached to an end/opening 71 (FIG. 5) of the port 70 in communication with the tissue collection chamber 50. The tubing, not shown, may further be connected to a cannula or liposuction instrument for collection of adipose tissue from a patient. As shown, the port 70 may have two or more connectors/openings 71, 72 to accommodate multiple surgical instrument connections and/or to provide variations in connector sizes for different tube diameters or instruments.

In order to draw tissue into the tissue collection chamber 50, a pressure differential between the tissue collection chamber 50 and exterior of the container (i.e., within the surgical tubing connected to the port 70) is created. In one embodiment, the pressure differential is created by connecting a negative pressure source to another port in fluid connection with the container 20. For example, in one embodiment, a negative pressure source, such as a hospital vacuum line, is connected to the port 80 in fluid connection with the filtrate collection chamber 60. Other ports may be provided and used to produce the pressure differential to draw tissue into the tissue collection chamber 60.

Once a desired amount of tissue is collected, the tissue may be processed (e.g., washed, concentrated, partially dried) before reimplantation, or the tissue may be implanted without further processing. In some embodiments, the tissue is washed one or more times. The tissue can be washed by contacting the tissue with fluid (e.g., saline, ringer's lactate, detergents, collagenase, stem cells, pH buffers.) The tissue can be contacted with fluid by transferring fluid into the tissue collection chamber. In one embodiment, the fluid is injected via the port 70. In that way, the fluid will serve to provide a mixing effect to enhance cleaning. It will be appreciated, however, that the washing or processing fluids can be inserted through other ports, e.g. through an upper surface of the container 20.

After or simultaneous with injection of washing fluids, filtrate (e.g., washing fluid and undesired materials in the tissue) can be removed through the filtrate collection chamber 60. In certain embodiments, the filtrate is removed by applying negative pressure to one or more ports 80 in communication with the filtrate collection chamber 60. It will be appreciated that a sloped or conical shaped filter can be beneficial by allowing removal of fluids through the filtrate collection chamber 60, while also assisting in directing tissue towards the opening 72 of port 70 for reimplantation.

After washing, or instead of washing, tissue may be processed to remove excess water and/or concentrate adipose cells. For example, in certain embodiments, additional negative pressure is used to pull a desired amount of water out of tissue within the tissue collection chamber, thereby increasing the concentration of adipose cells available per unit volume for implantation. After processing, the tissue can be transferred out of the tissue collection chamber 50 for reimplantation. A surgical instrument may be again connected to openings/connectors 71, 72 so that tissue can be transferred through the port 70 for reimplantation. Next, in order to facilitate transfer through the port 70, the flexible membrane 40 is caused to expand, thereby pushing the tissue towards the opening 74 of the port 70 and into an attached instrument for reimplantation. In addition, as the expanded membrane pushes the tissue against the walls of the filter, the excess fluid is removed from the tissue. In certain embodiments, a tube is connected to port 70 and fitted to a re-injection cannula and a valve. In certain embodiments, as the membrane expands, it pushes the tissue through the tube and reinjection cannula appended to port 80. In certain embodiments, the process according to the present disclosure permits pushing the tissue from the filter through the cannula at a constant pressure.

The flexible membrane 40 can be caused to expand in a number of ways. As described above, the flexible membrane 40 can be connected to at least one of an inner surface 14 of the container within the peripheral rim portion 12 and the peripheral rim portion 12 of the filter 30 to form a fluid-tight seal between at least a part of the at least one inner surface 14 and the first tissue collection chamber 50. In addition, the device 10 can comprise at least one port 90 in fluid communication with a cavity or space 41 formed between the membrane and container wall or inner surface 14 (FIG. 2B). In some embodiments, an opening 94 of the port 90 is within the cavity/space 41. During transfer of tissue into the tissue collection chamber 50, the port 90 may be closed. During transfer of tissue out of the chamber, the port 90 may be opened to allow fluid and/or air to enter the cavity/space 41 to expand the cavity and flexible membrane.

Additional methods may be used to increase the expansion force of the flexible membrane 40 to allow transfer of tissue out of the tissue collection chamber 50. For example, in one embodiment, negative pressure is again applied to the filtrate collection chamber 80 while the port 90 is opened, thereby creating a reduced pressure within the container 20 and causing the flexible membrane 40 to expand. In addition, or alternatively, pressurized fluid or air may be injected through the port 90 and into the cavity/space 41 to force the flexible membrane 40 to expand with a desire level of force.

It will be appreciated that expansion of the flexible membrane may also be used to facilitate tissue washing and removal of fluid. For example, in some embodiments, the opening 72 can be closed, and the flexible membrane 40 can be caused to expand to squeeze excess water or washing fluid out of tissue within the tissue collection chamber 60.

In certain embodiments, the method for harvesting, processing, and transferring adipose tissue, as described herein, is carried out as a single batch operation. In certain embodiments the method for harvesting, processing, and transferring adipose tissue, as described herein, is carried as a continuous operation.

What is claimed is:

1. A method for preparing tissue comprising:
   selecting a device comprising:
   a main container having at least one inner surface and a bottom wall;
   a filter having a sloped wall and a peripheral rim portion, wherein the filter is positioned within the main container such that the peripheral rim engages at least one inner surface of the main container to define a first tissue collection chamber and a second filtrate collection chamber, and wherein the filter sloped wall is attached to the bottom wall;
   at least one port passing through a portion of the bottom wall and in fluid communication with the first tissue collection chamber and an exterior of the main container, the at least one port having an opening within the first tissue collection chamber; and a flexible membrane attached at its periphery, the periphery of the flexible membrane attached to at least one of the filter and the at least one inner surface of the main container to define the first tissue collection chamber as a space between the flexible membrane and the sloped wall of the filter, and wherein the flexible membrane has sufficient flexibility to allow expansion of the flexible membrane into the first tissue collection chamber to force at least a portion of a tissue that may be contained in the first tissue collection chamber through the at least one port;

transferring tissue to the first tissue collection chamber;

processing the tissue within the first tissue collection chamber; and causing the flexible membrane to expand within the first tissue collection chamber to apply pressure to the tissue within the first tissue collection chamber to transfer the tissue out of the first tissue collection chamber through the at least one port in fluid communication with the first tissue collection chamber.

2. The method of claim 1, wherein transferring tissue to the first tissue collection chamber includes applying a suction pressure to at least one port in fluid communication with the device to draw tissue into the first tissue collection chamber.

3. The method of claim 2, wherein applying the suction pressure to at least one port to draw tissue into the first tissue collection chamber includes applying negative pressure to a port having an opening within the second filtrate collection chamber to produce a pressure differential between the first tissue collection chamber and the at least one port having an opening within the first tissue collection chamber.

4. The method of claim 1, wherein processing the tissue includes at least one of washing the tissue, concentrating the tissue, and removing a portion of water contained in the tissue from the tissue.

5. The method of claim 1, wherein processing the tissue includes washing the tissue by contacting the tissue with a washing fluid.

6. The method of claim 1, wherein the membrane is expanded by applying pressure to a space formed between the flexible membrane and the at least one inner surface of the container.

7. The method of claim 1, wherein the membrane is expanded by creating a pressure differential between an interior of the first tissue collection chamber and a space formed between the flexible membrane and the at least one inner surface of the main container.

8. The method of claim 7, wherein the pressure differential is created by applying negative pressure to the interior of the chamber.

9. The method of claim 1, further comprising removing water from the tissue prior to transferring the tissue out of the first tissue collection chamber.

10. The method of claim 9, wherein the water is collected in the second filtrate collection chamber.

11. The method of claim 9, wherein the water is removed by applying suction to the tissue in the first tissue collection chamber.

12. The method of claim 9, wherein the water is removed by expanding the flexible membrane while the at least one port in fluid communication with the first tissue collection chamber is closed, thereby applying pressure to the tissue with the flexible membrane.

13. The method of claim 1, wherein the tissue comprises an adipose tissue.

* * * * *